United States Patent [19]

Tong

[11] 4,075,207

[45] Feb. 21, 1978

[54] MICROBICIDAL/FUNGICIDAL THIAZOLOPYRAZINES

[75] Inventor: Yulan C. Tong, Walnut Creek, Calif.

[73] Assignee: The Dow Chemical Company, Midland, Mich.

[21] Appl. No.: 769,487

[22] Filed: Feb. 17, 1977

[51] Int. Cl.² ..................... C07D 513/04; A01N 9/14
[52] U.S. Cl. ................................ 260/250 BC; 71/90; 424/250
[58] Field of Search .................................. 260/250 BC

[56] References Cited

FOREIGN PATENT DOCUMENTS 1,175,243   8/1964   Germany ...................... 260/250 BC

OTHER PUBLICATIONS

"Chemical Abstracts", vol. 61, 1964, Col. 5668 f.

Primary Examiner—Alton D. Rollins
Assistant Examiner—James H. Turnipseed
Attorney, Agent, or Firm—Robert R. Stringham

[57] ABSTRACT

Thiazolopyrazines having growth inhibitory activity against microorganisms are of the formula

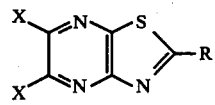

wherein X is —Br, —Cl or F and R is —H or —CH$_{3-x}$·Y$_x$, Y is —Br, —Cl, or F and $x$ is 0, 1, 2 or 3. These compounds also have utility as intermediates for the preparation of three-ring compounds which are highly active against microorganisms.

10 Claims, No Drawings

MICROBICIDAL/FUNGICIDAL THIAZOLOPYRAZINES

BACKGROUND OF THE INVENTION

Thiazolopyrazines are a known type of compound but no species of the above genus have been found to be disclosed in the literature. The known specific thiazolopyrazines most closely resembling those of the preceding formula are believed to be 6-bromothiazolopyrazine and its 2-methyl homologue. The former compound is disclosed, in Chemical Abstracts: 57, 2224(b), (1962), as having been prepared in the course of a structure proof and no biological utility is disclosed for it. The latter compound is disclosed in British Pat. No. 958,626 (1964); (C.A. 61, 5668 (1964)) as an intermediate for which no biological utility is given.

SUMMARY OF THE INVENTION

The present invention is a group of thiazolopyrazines having utility for inhibiting the growth of microorganisms. The compounds may be represented by the formula

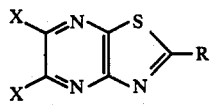

wherein X, independently in each occurrence, is —Br, —Cl or —F and R is H, or $CH_{3-x}Y_x$, Y is —Br, —Cl or —F, independently in each occurrence and $x$ is 0, 1, 2 or 3. Starting materials for the preparation of the compounds are 3-amino-5,6-dihalopyrazinethiols, which in turn can be made from corresponding tetrahalopyrazines by known methods. Some of the compounds also exhibit herbicidal, nematocidal or insecticidal activity, as well as microbicidal activity. The compounds may be used as intermediates for the preparation of 3-ring compounds, as by replacement of the X groups with, for example, —SH groups, followed by known types of ring closure reactions (condensations, ordinarily).

The compounds of the foregoing generic formula in which R is H, —$CH_3$, —$CH_2Cl$ and —$CF_3$ have the advantage of being preparable from more readily available starting materials than compounds in which R is —$CHBr_2$, —$CHClBr$, etc.

Those compounds of the invention in which R is $CF_3$ are the most active against microorganisms and also exhibit herbicidal activity, and are accordingly preferred. Also preferred are those compounds in which both X's are Cl, by reason of their greater ease of preparation and their suitability for use as intermediates. Thus, the compound in which both X's are Cl and R is $CF_3$ is particularly preferred.

DETAILED DESCRIPTION

The compounds of the present invention are crystalline solids, some of which are colorless (white) and others of which are of various colors (yellow, brown, green, orange, etc.). They are soluble in common organic solvents and range in melting point from about 50° C. to about 150° C.

Two principal methods may be employed for the preparation of the compounds of the invention. Those compounds in which R is H may be made by condensing a 3-amino-5,6-dihalopyrazine thiol with triethylorthoformate or with a lower alkyl formate. Those compounds in which R is methyl or halomethyl may be prepared by condensing the aminodihalopyrazinethiol with acetic anhydride, acetyl chloride or a halogen substituted anhydride or chloride. In addition, the products of the preceding condensation reactions can be modified by halogenation and/or halogen exchange reactions.

The preceding condensation reactions are carried out at reflux and generally in a relatively high-boiling medium such as toluene or xylene. When triethylorthoformate is employed in the reaction, use of an additional solvent may be dispensed with. Reaction times of from about 5 to about 24 hours have been found suitable. When water is evolved in the course of the reaction, it is conveniently removed from the reaction zone by use of a Dean-Starks type water trap in conjunction with an overhead condenser. Work-up procedures are generally quite simple, as by cooling and filtering or by stripping under reduced pressure and then recrystallizing or subliming the crude product so obtained.

Compounds of the invention in which the two X's are different may be made by reacting the corresponding dichloro compound, in a polar solvent, with a bromide or fluoride source material such as HBr, KF, etc. Similarly, the corresponding dibromo compound can be reacted with a fluoride source material. Compounds in which both X's are fluoride can also be made by such reactions, starting with the corresponding dihalo compounds in which each halogen is either Cl or Br, independently. Methods of carrying out such reactions with halogen-substituted N-heterocycles are well known.

Direct halogenation may be employed for introduction of chlorine or bromine in a 2-methyl group and exchange reactions may be carried out between fluoride and Cl or Br substituents on 2-methyl groups.

Those skilled in the art will recognize that the sequence in which halogenation and exchange reactions (when both are contemplated) should be carried out will depend on the particular endproduct to be prepared. It will also be recognized that mixtures of isomeric products may result when only one of two identical X's is replaced by a different halogen. Such mixtures may be utilized as such or subjected to conventional isomer separation techniques.

EXAMPLES

The aminotrichloro- and aminotribromopyrazine starting materials used in the following examples were made from tetrachloro- and tetrabromopyrazine, respectively, in the manner reported by G. Palamidessi and F. Luini, Farmaco Ed. Sc., 21, 811 (1966).

EXAMPLE 1

Preparation of 2-Amino-5,6-dichloro-3-mercaptopyrazine

A mixture of 19.9 g. (0.1 mol.) of aminotrichloropyrazine, 25.2 g. (0.105 mol.) of sodium sulfide nonahydrate in 500 ml. of 2-propanol was heated to boiling under reflux for 5 hours. After cooling, the reaction mixture was filtered. The filtrate was neutralized with hydrochloric acid and filtered. The solid was washed with water and dried to give 11.4 g. (58% yield) of product. Anal. Calcd. for $C_4H_3Cl_2N_3S$: C, 24.5; H, 1.54; N, 21.4. Found: C, 24.9; H, 1.7; N, 21.0.

This compound did not have a well defined melting point. Upon heating, it changed color at about 150° C., became black and stayed solid. There was a sharp exotherm at 170° C. TGA (Thermal Gravimetric Analysis) showed the loss of 20% of weight around 150°–200° C.

EXAMPLE 2

Preparation of 3-Amino-5,6-dibromopyrazinethiol

Aminotribromopyrazine was prepared, by the same procedure reported for the trichloro analog, from tetrabromopyrazine.

Using the same procedure as above, 30 g. of aminotribromopyrazine, and 24 g. of sodium sulfide nonohydrate in 500 IPA gave 13.5 g. (53% yield) of the desired compound.

Anal. Calcd. for $C_4H_3Br_2N_3S$: C, 16.86; H, 1.06; N, 14.74. Found: C, 17.55; H, 1.21; N, 14.89.

EXAMPLE 3

Preparation of 2-Chloromethyl-5,6-dichlorothiazolo-(4,5-b)pyrazine

A mixture of 10 g. (0.05 moles) of 5,6-dichloro-2-thio-3-aminopyrazine, 10 g. (0.06 moles) of chloroacetic anhydride and 500 ml. of toluene were placed in a 1 liter round bottom flask fitted with a "Dean-Starks" water trap, an efficient condenser and magnetic stirring. The mixture was refluxed for 5 hours. The flask was cooled, the magnetic stirring bar removed, and the contents taken to dryness on a rotary evaporator under reduced pressure. The product was recrystallized from methanol; 10.5 g. (83% yield), m.p. 126°–8° C.

Anal. Calcd. for $C_6H_2Cl_3N_3S$: C, 28.31; H, 0.79; N, 16.51. Found: C, 28.00; H, 0.89; N, 16.55.

EXAMPLE 4

Preparation of 5,6-Dichloro-2-methyl-thiazolo(4,5-b)pyrazine

A mixture of 9.8 g. (0.05 mol.) of 2-amino-5,6-dichloro-3-mercaptopyrazine and 5.1 g. (0.05 mol.) of acetic anhydride in 100 ml. of xylene was heated at 110° C. for 1 hour. The reaction mixture was cooled, another 5.1 g. of acetic anhydride was added and heating at 110° C. was continued for 15 hours. The reaction mixture was concentrated under reduced pressure to give a dark oil, which solidified under isopropanol-hexane while cooling in ice. The dark solid was purified by sublimation to give 7 g. (64% yield) of white solid, m.p. 58°–60° C.

Anal. Calcd. for $C_6H_3Cl_2N_3S$: C, 32.8; H, 1.4; N, 19.1. Found: C, 32.9; H, 1.5; N, 19.6.

EXAMPLE 5

Preparation of 5,6-Dichloro-2-trifluoromethylthiazolo(4,5-b)pyrazine

A mixture of 4.9 g. (0.025 mol.) of 2-amino-5,6-dichloro-3-mercaptopyrazine and 4 ml. of trifluoroacetic anhydride in 50 ml. of xylene was heated to boiling under reflux for 1 hour. Another 4 ml. of trifluoroacetic anhydride was added and heating continued for another 4 hours. The reaction mixture was evaporated to dryness to give 3.5 g. of green solid. Infra-red analysis indicated a mixture of an amide and the desired product. It was recrystallized from 50 ml. of 2-propanol to give 2.5 g. (36% yield) of green crystalline product, m.p. 122°–124° C.

Anal. Calcd. for $C_6Cl_2F_3N_3S$: C, 26.3; N, 15.3. Found: C, 26.4; N, 15.8.

EXAMPLE 6

Preparation of 5,6-Dichlorothiazolo(4,5-b)pyrazine

To 100 ml. of triethyl orthoformate was added 9.8 g (0.05 mole) of 2-amino-5,6-dichloro-3-mercaptopyrazine. The whole was heated to boiling under reflux for 20 hours, cooled to room temperature and filtered, washed with petroleum-ether and dried to give 7.7 g. (75% yield) of the desired product, m.p. 124°–5° C.

Anal. Calcd. for $C_5HCl_2N_3S$: C, 29.14; H, 0.49; N, 20.39. Found: C, 28.90; H, 0.72; N, 20.22.

EXAMPLE 7

Preparation of 5,6-Dibromothiazolo(4,5-b)pyrazine

Fifty ml. of triethylorthoformate and 8.6 g. of 3-amino-5,6-dibromopyrazinethiol were mixed and heated to boiling under reflux for 22 hours. The reaction mixture was then concentrated under reduced pressure and diluted with petroleum-ether. The resulting precipitate of yellowish brown crystalline material weighed 6.7 g. (73% yield), m.p. 142°–4° C.

Anal. Calcd. for $C_5HBr_2N_3S$: C, 20.36; H, 0.34; N, 14.25. Found: C, 20.82; H, 0.46; N, 14.19.

UTILITY

The compounds of the present invention are useful as biocides. They are generally active as microbicides, fungicides and industrial preservatives. Some of the compounds show a useful degree of activity as herbicides and/or insecticides.

The compounds of the invention can be applied to the aerial portions of many growing plants to control leaf-attacking fungal organisms or dispersed in soil or applied to plant seeds to control the root and seed attacking organisms of mold and damping off. In still other operations they can be applied to orchard floor surfaces to control over-wintering spores of many fungal organisms. In still further operations, the compounds of the invention or compositions containing them as toxic constituents can be included in and on plaster, ink, wallboard, textiles, paper, adhesives, soaps, synthetic detergents, cutting oils, polymeric materials, embalming fluids, oil paints and latex paints to prevent the attack of various fungal pests and the subsequent economic loss due to the degradation of such products by microorganisms. Also, the compounds can be distributed in textiles, cellulosic materials or in grain or can be employed in the impregnation of wood and lumber to preserve and protect such products from the attack of the organisms of rot, mold and decay. They also can be employed as a toxicant to control insect pests.

The exact concentration of the toxicant to be employed in the treating compositions is not critical and may vary considerably provided the required dosage of the effective agent is supplied in the ink, adhesive, soap, cutting oil, polymeric material, paint, textile, paper, wood or growth medium or upon plant foliage or insects. The concentration of toxicant in liquid compositions generally is from about 0.0001 to 50 percent by weight. Concentrations up to 95 percent by weight are oftentimes conveniently employed, particularly in concentrate compositions. In dusts, the concentrations of the toxicant can be from about 0.1 to 95 percent by weight. In compositions to be employed as concentrates, the toxicants can be present in a concentration of from 5 to 98 percent by weight. For use as a foliar spray or in seed treatment, it is often convenient to apply the compounds as wettable powders.

The compounds may be used with a wide variety of oils, resin, solvents, pigments and coating additives in formulating organic film-forming compositions having mildew resistance. The more common types of exterior coatings for which such compounds are useful as fungicides include the drying oils, alkyds and in latex-type paints. The film-forming vehicles include the triglyceride esters of unsaturated fatty acids such as linseed oil or soya oil; esters of polycarboxylic acids with polyols, such as reaction products of phthalic anhydride with glycerol or pentaerythritol; oil-modified alkyds; modified phenolic resins, such as aldehyde condensations; melamine resins; synthetic elastomeric latexes; homopolymers or copolymers of olefinically unsaturated compounds, including vinyl acetates and acrylic resins; urethane resins; ether resins and numerous other conventional coating vehicles. Typical pigments which can be combined in exterior paints comprise titanium dioxide, alkaline earth carbonates and silicates, bentonite, mica, metal oxides, carbon, etc. Solvents and co-solvents are used conventionally in both organic-thinned or water-thinned coating compositions, for instance, mineral spirits, polyols, benzoids, etc. Numberous additives can be incorporated in the antifungal paints for suppressing foam, for plasticizing the dried films, for emulsifying latexes, or for accelerating the film cure.

While the antifungal additive is usually incorporated directly into a coating to be applied as a top coat, some organic coatings can be adequately protected by using the antifungal additive in a primer or intermediate coat. Migration into an adjacent layer from a substrate containing a fungicide can be an effective means for controlling mildew in some applications. A relatively higher local concentration of fungicidal agent may be necessary under such conditions. Direct application of the fungicide with an inert carrier over the organic nutrient surface may be used to protect against fungus growth, but this method may not be desirable for exterior weathered surfaces due to erosion. Some interior surfaces in food processing rooms, such as bakeries, breweries, meat packing plants, etc., also suffer from mildew growth due to extreme conditions of humidity or temperature. Here the weathering effect is not such an important factor, but the use of a fungicide is desirable.

Mildew growth on exterior organic coatings is attributed to several fungi. The relative importance of different species of fungi is climatically dependent; but, Pullularia species usually account for the major number of fungus colonies on painted surfaces in the United States. In warm, moist climates such as the Gulf areas around the 30th parallel, Pullularia species account for about 75% to over 90% of mildew growth. North of the 40th parallel this species amounts to more than half the growth. In the warmer moist areas, Alternaria species, Cladosporium species, and Penicillium species are secondary causes of discoloration. In the northern climates Aspergillus species also is a secondary mildew fungus.

A number of other micro-organisms, such as Rhodotorula (yeast), Monilia, Mucor and Botrytis, are minor causes of mildew. An organic surface that is a nutrient for some fungi may not be a nutrient for others. Generally, a nutrient for other fungi will also support Pullularia growth. Alternaria occurrence is higher in latex paints, whereas Cladosporium does not thrive on a typical latex film. Rhodotorula is associated mostly with drying oil paint vehicles and areas protected from weathering.

The preferred concentrations of the compounds of the invention in the dry coating films is from the minimum inhibitory concentration up to about 2 percent by weight. Higher concentrations may be employed but generally are of no greater benefit.

EXAMPLE 8

In Vitro Fungicide/Microbicide Tests

In a representative operation, each of the compounds listed in Table 1 was tested by incorporating it as the sole toxicant in each of from fourteen to twenty nutrient agars, each inoculated with a different organism from the following list. The results are given in the Table.

| No. | Organism | No. | Organism |
|---|---|---|---|
| 1 | Staphylococcus aureus | 14 | Ceratocystis ips |
| 2 | Escherichia coli | 15 | Cephaloascus fragans |
| 3 | Candida Albicans | 16 | Trichoderm sp. Madison P-42 |
| 4 | Tricophton mentagrophytes | 17 | Pseudomonas aeruginosa |
| 5 | Bacillus subtilis | 18 | Aspergillus nigricans |
| 6 | Aerobacter aerogenes | 19 | Candida albicans NIH |
| 7 | Aspergillus terreus | 20 | Kleb pneumoniae M-J mid. hosp. |
| 8 | Candida pelliculosa | 21 | Penicill chrysogesum |
| 9 | Pullularia pullulans | 22 | Serrafia marcessens NIH |
| 10 | Salmonella typhosa | 23 | Torulopsis specie med. col. VI |
| 11 | Pseudomonas sp. strain 10 | 24 | Aspergillus fumig med. col. VI |
| 12 | Mycobacterium phlei | 25 | Aspergillus niger |
| 13 | Rhizopus nigricans | | |

TABLE 1

| Compound | Conc'n in Agar p.p.m. | Numbers of Organisms Whose Growth Was: | |
|---|---|---|---|
| | | Stopped | Restricted |
| 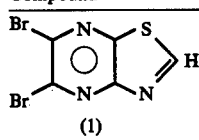 (1) | 50 | 4,5,10 | |
| | 100 | 1,3,8,19, 24,25 | 2 |
| | 500 | 2,9,12–14, 16,20,21 | |
| 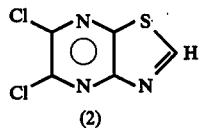 (2) | 50 | 5,11,15, 19,21,25 | |
| | 100 | 2–4,8–10, 14,16 | 12 |
| | 500 | 1,3,6,11, 15,17,20, 22,23 | |
| 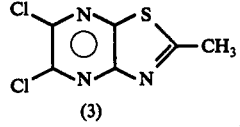 (3) | 100 | | 4,7 |
| | 500 | 7,13 | |

TABLE 1-continued

| Compound | Conc'n in Agar p.p.m. | Numbers of Organisms Whose Growth Was: | |
|---|---|---|---|
| | | Stopped | Restricted |
| Cl-[structure]-CF₃ (4) | 1 10 100 500 | 4,7 1,5,8,9, 12-16 3 | 4 8,9,14,15 |
| Cl-[structure]-CH₂Cl (5) | 1 5 10 50 | 14,21 8,9,24 1,3,5,10, 16,19,23 | 4 |

EXAMPLE 9

Pre-emergence Herbicide Tests

Several of the compounds in the preceding table exhibited pre-emergent herbicidal activity when applied as aqueous drenches to soil planted with seeds of certain plants, as summarized in Table 2 below.

TABLE 2

| Compound | Application Rate | Plant | % Control* |
|---|---|---|---|
| 2 | 10 lbs/acre | Pig Weeds-ETCC | 100 |
| 3 | 20 lbs/acre | Pig Weeds-ETCC | 50 |
| | 4000 ppm | Crabgrass | 50 |
| | 4000 ppm | Barnyard Grass | 45 |
| 4 | 20 lbs/acre | Pig Weeds-ETCC | 100 |
| | 2 lbs/acre | " | 40 |
| | 2 lbs/acre | Wild Mustard-Charlock | 100 |
| | 2 lbs/acre | Cotton | 30 |
| | 20 lbs/acre | Bindweed | 60 |
| | 20 lbs/acre | Yellow Foxtail | 100 |

*After two weeks.

EXAMPLE 10

Nematocide Tests

Compound 5 gave 90 percent control of rootknot nematodes when mixed as a 2400 ppm aqueous drench with a root knot nematode-infested soil which was subsequently planted with cucumber plants (control reported in comparison to damage in same test period, 3 weeks, to plants in untreated, nematode infested soil).

(Compound 5 has also shown some anthelmintic activity against trichostronglylid in mice.)

EXAMPLE 11

Insecticide Tests

Compound 2 gave 40 percent control of Two-Spotted Spider Mite when applied at a concentration of 500 ppm in the manner described below. Compound 5, when similarly tested against Beet Army Worm Larvae at a concentration of 400 ppm, gave 100 percent control.

Immature test plants are infested with the insect pest, dipped in an aqueous dispersion of the test chemical and planted in vermiculite. More of the dispersion is injected into the vermiculite around the roots of the plant. (If necessary, the insects are confined during dipping.) Percent control is in comparison with untreated infestations on identical host plants, allowance being made for natural mortality rates.

The foregoing Examples are for purposes of illustration and are not to be construed as limiting the scope of the present invention to an extent inconsistent with the claims appended with these specifications.

What is claimed is:

1. A compound of the formula

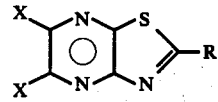

wherein, X, independently in each occurrence, is Br, Cl or F, R is H or $CH_{3-x}Y_x$, Y is Br, Cl or F, independently in each occurrence, and $x$ is 0, 1, 2 or 3.

2. A compound of claim 1 in which X is Br or Cl, the same in both occurrences.

3. A compound of claim 1 in which R is H, —CH₃, —CH₂Cl or —CF₃.

4. A compound of claim 2 in which R is H, —CH₃, —CH₂Cl or —CF₃.

5. A compound of claim 4 in which X is Cl.

6. The compound of claim 4 in which X is Br and R is H.

7. The compound of claim 5 in which R is H.

8. The compound of claim 5 in which R is CH₃.

9. The compound of claim 5 in which R is CH₂Cl.

10. The compound of claim 5 in which R is CF₃.

* * * * *